United States Patent [19]

Rammelt et al.

[11] 4,400,546
[45] Aug. 23, 1983

[54] PROCESS FOR THE PREPARATION OF HEXAFLUOROACETONE AND DIRECT USE OF THE SOLUTION OBTAINED BY THE PROCESS

[75] Inventors: Peter-Paul Rammelt; Günter Siegemund, both of Hofheim am Taunus, Fed. Rep. of Germany

[73] Assignee: Hoechst Aktiengesellschaft, Frankfurt am Main, Fed. Rep. of Germany

[21] Appl. No.: 328,818

[22] Filed: Dec. 9, 1981

[30] Foreign Application Priority Data

Dec. 11, 1980 [DE]  Fed. Rep. of Germany ....... 3046604

[51] Int. Cl.³ .............................................. C07C 45/58
[52] U.S. Cl. .................................. 568/386; 568/728; 570/142
[58] Field of Search .......................... 508/386, 419, 393

[56] References Cited

U.S. PATENT DOCUMENTS 3,213,134 10/1965 Morin .................................. 568/386
3,321,515  5/1967 Moore et al. ....................... 568/335
3,385,904  5/1968 Pavlik .................................... 560/87
3,391,119  7/1968 Anderson ............................. 568/385
3,787,489  1/1974 Antonini et al. .................... 568/393
4,238,416 12/1980 Tohzuka et al. .................... 568/419

OTHER PUBLICATIONS

Knunyants et al., I52 Akad Nawk SSSR, Ended, vol. 4, pp. 647–653 (1960).
Chem. Abstracts No. 108144x, vol. 67, p. 10180 (1967).

*Primary Examiner*—James H. Reamer
*Attorney, Agent, or Firm*—Curtis, Morris & Safford

[57] ABSTRACT

Hexafluoroacetone is prepared by a rearrangement of hexafluoropropene epoxide at an elevated temperature in the presence of hydrogen fluoride as a catalyst and, if appropriate, also as a solvent. In many cases the solution of hexafluoroacetone in hydrogen fluoride obtained in this process can be directly employed without further working-up or purification in further reactions of hexafluoroacetone, for example with phenol and/or o-cresol.

6 Claims, No Drawings

PROCESS FOR THE PREPARATION OF HEXAFLUOROACETONE AND DIRECT USE OF THE SOLUTION OBTAINED BY THE PROCESS

Hexafluoroacetone $CF_3COCF_3$ is a valuable intermediate and final product in various fields. Hexafluoroacetone is thus of importance as an intermediate product, for example in the copolymerization of perfluoroolefins and for the preparation of plant protection agents or of crosslinking agents for fluorine-containing elastomers. Examples of crosslinking agents of this type are the diphenols 4,4'-(hexafluoroisopropylidene)-diphenol=-hexafluoro-2,2-bis-(4-hydroxyphenyl)-propane (I) and 4,4'-(hexafluoroisopropylidene)di-o-cresol=hexafluoro-2,2-bis-(3-methyl-4-hydroxyphenyl)-propane (II), which can be obtained, according to I. L. Knunyants et al. [Isz. Akad. Nauk SSSR, Otdel. Khim. Nauk 4, 686–692 (1960)—English edition pages 647–653, in particular 649–650], by reacting hexafluoroacetone with phenol or o-cresol in anhydrous hydrogen fluoride:

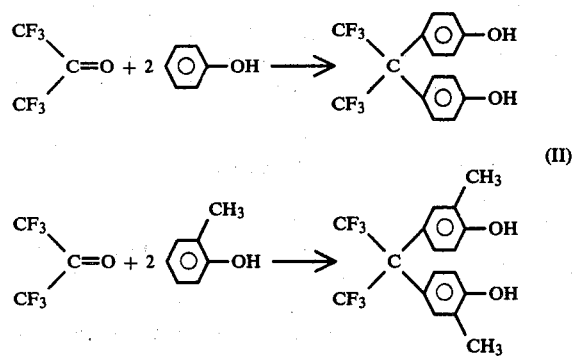

Hexafluoroacetone is also important as a final product, inter alia as a solvent for fluorine-containing polymers and the like.

The preparation of hexafluoroacetone is effected advantageously by a rearrangement (isomerization) of hexafluoropropene epoxide, which in turn can be obtained advantageously, for example by an anodic oxidation of hexafluoropropene by processes, disclosed in German Pat. No. 2,460,468 and its Addition No. 2,658,328, in an electrolysis cell in accordance with German Pat. No. 2,658,382.

It is known that one way of carrying out the rearrangement of hexafluoropropene epoxide to give hexafluoroacetone is in the presence of antimony pentafluoride $SbF_5$ at temperatures between about $-15°$ and $+350°$ C. (U.S. Pat. No. 3,213,134); however, the only example dealing with this rearrangement (No. 5) does not contain any indications of yield. This U.S. patent specification points out in particular that the rearrangement is to be carried out in the absence of hydrogen fluoride, since otherwise—that is to say in the presence of hydrogen fluoride—mainly the corresponding alcohol (by the addition hydrogen fluoride) is allegedly produced.

The formation of alcohol due to the addition of hydrogen fluoride to perfluorinated epoxides is exploited in a process for the preparation of perfluorinated tertiary alcohols by the reaction of perfluoroisoalkene-1,2-epoxides having at least 4 and at most 20 C atoms with anhydrous hydrogen fluoride (if appropriate in the presence of catalysts, such as $SbF_5$, CsF and the like) at temperatures between about $+20°$ and $+350°$ C. in accordance with U.S. Pat. No. 3,385,904. This process can be represented by the following reaction equation:

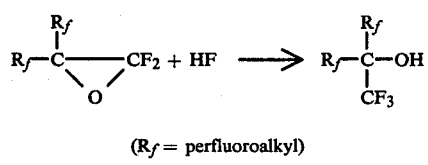

($R_f$ = perfluoroalkyl)

A further known method for the rearrangement of hexafluoropropene epoxide to give hexafluoroacetone employs so-called Lewis acids (these are electron acceptor compounds) as catalysts (U.S. Pat. No. 3,321,515). Certain acid metal oxides, metal halides and metal carbonyls may be mentioned as possible Lewis acids for this purpose. In the examples which refer to the rearrangement of hexafluoropropene oxide to give hexafluoroacetone (No. 1, 3 and 4), hexafluoroacetone yields of between about 50 and 80% of theory are achieved when acid aluminum oxide or aluminum chloride are used as catalysts.

When so-called Lewis bases (these are electron donor compounds) are used as catalysts, the rearrangement of hexafluoropropene epoxide leads in another direction, namely to the formation of the corresponding acid fluoride. The reaction diagram below illustrates the two rearrangement possibilities of hexafluoropropene epoxide, depending on whether a Lewis acid or a Lewis base is used as catalyst:

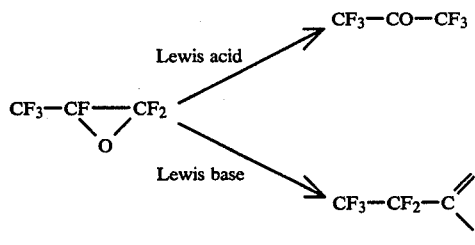

Fluorine compounds which are capable of splitting off fluorine ions, such as, for example, KF, $KHF_2$ and the like, are mentioned, inter alia, as Lewis bases. In this reaction the fluorine ions are said to be responsible for the catalytic activity of the compounds as Lewis bases. Even compounds which are normally considered to be Lewis acids, but which are capable of splitting off fluorine ions, are said to act as Lewis bases, in the rearrangement in question, because of the detachable fluorine ions.

Hexafluoroacetone which has been prepared according to the known processes by a rearrangement of hexafluoropropene epoxide in the presence of catalysts of course initially still contains the catalysts employed, a fact which is inconvenient for various applications of hexafluoroacetone. In these cases the catalyst has to be separated off. However, particularly when the catalysts are present in dissolved form, such catalyst separation is not without complications and frequently is only possible (if at all) with considerable effort.

One object of the present invention is an improved process for the preparation of hexafluoroacetone whereby the reaction product no longer contains any catalyst which is inconvenient for the further use of the hexafluoroacetone.

This object is achieved in accordance with the invention by the use of hydrogen fluoride as catalyst and, if appropriate, as the solvent.

The invention is in a process for the preparation of hexafluoroacetone by rearrangement of hexafluoropropene epoxide at an elevated temperature in the presence of an acid catalyst, which process comprises using hydrogen fluoride as acid catalyst and, if appropriate, as solvent.

This procedure makes it possible to achieve hexafluoroacetone yields of over 90% of theory, at high (almost quantitative) conversions and at a high selectivity. This was extraordinarily surprising, because it had to be assumed from the relevant prior art that hexafluoropropene epoxide in the presence of hydrogen fluoride produces in part (via the addition of hydrogen fluoride) the corresponding perfluorinated alcohol (see U.S. Pat. No. 3,213,134 and U.S. Pat. No. 3,385,904), in part the corresponding acid fluoride see U.S. Pat. No. 3,321,515; fluorine ions directing the rearrangement in the direction of the acid fluoride.

In order to ensure a sufficiently high conversion, when carrying out the process according to the invention, hydrogen fluoride is advantageously employed not just in a catalytic quantity, but in excess—that is to say also as solvent. The molar ratio of hexafluoropropene epoxide to hydrogen fluoride is preferably 1 to at least about 4, preferably 1 to about 7 to 9. An even greater excess of hydrogen fluoride is not in itself harmful, but it does not constitute an advantage either owing to the more elaborate working-up procedure that would be necessary.

To ensure a sufficiently high rate of reaction and a sufficiently high conversion the reaction temperature should be above about 65° C.; it is preferably between about 70° and 150° C., in particular between about 90° and 125° C. Higher temperatures are in themselves possible but they lead to the formation of secondary products, such as, for example, trifluoroacetyl fluoride and trifluoromethane, and therefore to a reduction of the hexafluoroacetone yield.

The reaction pressure as such is not critical. It is dependent on the amounts present of the reactants hexafluoropropene epoxide and hydrogen fluoride, relative to the capacity of the reactor, the weight ratio between hexafluoropropene epoxide and hydrogen fluoride and the reaction temperature used. In general it is at the start of the reaction between about 30 and 50 bar and normally decreases towards the end of the reaction to about 20 bar and less.

The process can be carried out in an autoclave with or without a stirring device. The apparatus required for carrying out the reaction can consist of all sufficiently corrosion-resistant materials, such as, for example, iron, chromium, nickel and noble metals and their alloys.

To ensure a sufficiently high conversion in the temperature range indicated, the reaction period is in general between about 10 and 25 hours, preferably between about 20 and 24 hours.

The process according to the invention is in general carried out by loading hexafluoropropene epoxide and hydrogen fluoride into an autoclave and heating the mixture at the reaction temperature until the reaction is complete. The pressure which develops due to the vapor pressure of the mixture decreases steadily as the reaction progresses (probably because of the formation of a labile addition product from HF and hexafluoroacetone) and can be used as a rough indication of the end of the reaction. At the end of the reaction the hexafluoroacetone is present in a solution in hydrogen fluoride and can be made further use of either by separating off the hydrogen fluoride (for example by washing with oleum) or in the form of a solution in hydrogen fluoride. Since numerous reactions involving hexafluoroacetone are carried out in hydrogen fluoride as solvent, in many cases the reaction of the solution obtained by the process according to the invention can be employed advantageously directly as it is for the corresponding further reactions, without the hexafluoroacetone having to be isolated.

In contrast to the comparable processes of the relevant prior art, the process according to the invention has the advantage-in particular when the reaction solution is employed directly for further reactions of hexafluoroacetone in hydrogen fluoride-that there is no need to remove any catalyst which may be inconvenient in the further reactions. In addition, the process always produces higher yields than are obtained by the known processes.

It is particularly advantageous to use the reaction solution obtained by the process according to the invention directly, that is to say without any sort of working-up procedure or purification, for a further reaction with phenol or o-cresol in accordance with Knunyants et al., loc. cit. An example of a possible procedure is to rearrange hexafluoropropene epoxide at around 100° C. in an about 8-fold molar amount of hydrogen fluoride in a pressure vessel, thereafter to add the required amount of phenol or o-cresol and to carry out the reaction to give hexafluoro-2,2-bis-(4-hydroxyphenyl)-propane or hexafluoro-2,2-bis-(3-methyl-4-hydroxyphenyl)-propane respectively at the same temperature. In the working-up the hydrogen fluoride is distilled off and it can be re-used in further reactions. The reaction product hexafluoro-2,2-bis-(4-hydroxyphenyl)-propane or hexafluoro-2,2-bis-(3-methyl-4-hydroxyphenyl)-propane remains as a solid substance and it can be purified in a customary manner.

The invention will now be explained in greater detail in the examples below.

EXAMPLE 1 TO 6

These examples explain the effect of temperature, of the molar ratio of hexafluoropropene epoxide to hydrogen fluoride and of the reaction period, on the rearrangement of hexafluoropropene epoxide.

The rearrangement was carried out in a 250 ml capacity steel autoclave, which was filled with hexafluoropropene epoxide, which contained about 0.3 mole % of hexafluoropropene and up to 4 mole % of cyclo-hexafluoropropane, and hydrogen fluoride. The rearrangement was initiated by warming the reaction vessel, with shaking, to the desired reaction temperature. At the end of the desired reaction period the reaction product was cooled to 40°-50° C. and it was washed with 65% strength oleum to remove hydrogen fluoride. The composition of the reaction product after the wash with oleum is shown in Table 1.

TABLE 1

| Example | Hexa-fluoro-propene epoxide g | Hydrogen fluoride g | Molar ratio HF:HFPO* | Reaction temperature °C. | Reaction period hours | Composition of the reaction product in mole % | | | | | | | Conversion % | Selectivity % |
|---|---|---|---|---|---|---|---|---|---|---|---|---|---|---|
| | | | | | | Hexa-fluoro-acetone | HFPO* | $CF_3$-COF | $CHF_3$ | $C_3F_6$ | Cyclo $C_3F_6$ | Unknown component | | |
| 1 | 110 | 70 | 5.3 | 85 | 5 | 2.6 | 95.7 | <0.3 0.1 | | <0.3 | 1.7 | 0.1 | 2.7 | 96.3 |
| 2 | 100 | 50 | 4.2 | 100 | 19 | 61.7 | 33 | 0.6 0.3 | | <0.3 | 3.3 | 1.1 | 65.9 | 96.9 |
| 3 | 100 | 110 | 9.1 | 100 | 10 | 88 | 7.6 | 0.8 0.2 | | 0.2 | 1.1 | 2.2 | 92.3 | 96.5 |
| 4 | 100 | 110 | 9.1 | 100 | 15 | 92.4 | 4.2 | <0.3 0.2 | | <0.3 | 1.8 | 1.1 | 95.7 | 98.3 |
| 5 | 100 | 100 | 8.3 | 100 | 19 | 92.5 | 0.9 | 0.3 0.1 | | 0.2 | 0.8 | 5.5 | 99.1 | 94.3 |
| 6 | 110 | 100 | 7.6 | 150 | 19 | 68.2 | 2.4 | 17.8 4.7 | | 0.5 | 2.4 | 4 | 97.5 | 72.0 |

*HFPO = Hexafluoropropene epoxide

EXAMPLE 7

100 g of hexafluoropropene epoxide, which contained about 0.3 mole % of hexafluoropropene and about 0.6 mole % of cyclo-hexafluoropropane, and 100 g of hydrogen fluoride were filled into a 250 ml capacity steel autoclave and the mixture was heated with shaking for 24 hours at 100° C. The cooled reaction product at 40°–50° C. was washed with 65% strength oleum to remove hydrogen fluoride and it was then condensed in a cooled receiving flask at −78° C. to give 79 g. The reaction product had the following composition (in mole %):

| Hexafluoro-acetone | Hexafluoro-propene epoxide | $CF_3$—COF | $CHF_3$ | $C_3F_6$ | cyclo-$C_3F_6$ | Unknown component | Conversion % | Selectivity % |
|---|---|---|---|---|---|---|---|---|
| 95.3 | 1.1 | <0.2 | <0.3 | <0.3 | 2.2 | 1.1 | 98.9 | 98.9 |

EXAMPLE 8

A mixture of 228 g of hexafluoropropene epoxide and 72 g of hexafluoropropene, and also 220 g of hydrogen fluoride were filled into a 1 liter capacity stainless steel autoclave without a stirring device and the mixture was heated for 20 hours at 100° C. The reaction product, which consisted of a solution of hexafluoroacetone in hydrogen fluoride, was transferred by exploiting its own vapor pressure to a 2.7 liter capacity nickel autoclave, which already contained 258 g of phenol, and the resulting mixture was heated for 8 hours at 100° C. After the hydrogen fluoride and the hexafluoropropene, which did not take part in the reaction, had been distilled off, 399 g of hexafluoro-2,2-bis-(4-hydroxyphenyl)-propane were obtained. This corresponds to a yield of 86.4% of theory.

We claim:

1. In a process for the preparation of hexafluoroacetone by conversion of hexafluoropropene epoxide the improvement which comprises reacting hexafluoropropene epoxide with at least a catalytic amount of hydrogen fluoride as catalyst.

2. The process of claim 1 wherein hexafluoropropene epoxide is reacted with hydrogen fluoride at a molar ratio of 1 mole epoxide per about 4 to 9 moles hydrogen fluoride.

3. The process of claim 2 wherein said molar ratio is 1 mole epoxide per about 7 to 9 moles hydrogen fluoride.

4. The process of claim 1 wherein said reaction is conducted at a temperature in the range of about 60° C. to 150° C.

5. The process of claim 1 wherein said reaction is conducted at a temperature in the range of about 90° C. to 125° C.

6. The process of claim 1 wherein said conversion is conducted in the presence of excess hydrogen fluoride sufficient to achieve a process yield of at least 90 percent.

* * * * *